Figure 1:
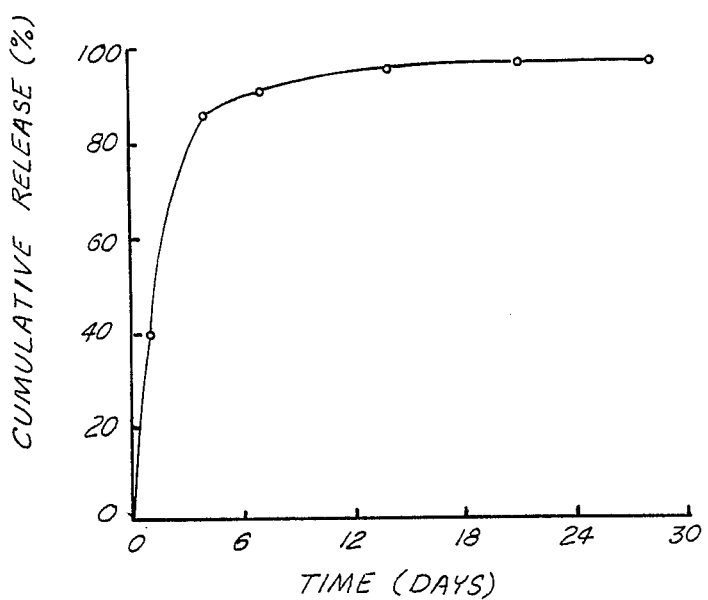

United States Patent [19]

Schacht et al.

[11] Patent Number: 4,975,280
[45] Date of Patent: Dec. 4, 1990

[54] BIOERODABLE SUSTAINED RELEASE IMPLANTS

[75] Inventors: Etienne Schacht, Staden; Jan Crommen, Ghent, both of Belgium

[73] Assignee: Ethyl Corporation, Richmond, Va.

[21] Appl. No.: 299,085

[22] Filed: Jan. 23, 1989

[51] Int. Cl.$^5$ .................................. A61K 9/00
[52] U.S. Cl. .................... 424/428; 424/422; 424/424; 424/425; 424/426; 424/486
[58] Field of Search ............ 424/426, 422, 425, 424, 424/428, 484, 486

[56] References Cited

U.S. PATENT DOCUMENTS

| | | | |
|---|---|---|---|
| 4,249,531 | 2/1981 | Heller et al. | 424/426 |
| 4,347,234 | 8/1982 | Wahlig et al. | 424/426 |
| 4,351,337 | 9/1982 | Sidman | 424/426 X |
| 4,638,045 | 1/1987 | Kohn et al. | 424/426 X |
| 4,639,366 | 1/1987 | Heller | 424/78 X |

FOREIGN PATENT DOCUMENTS

61/109800 5/1986 Japan .................. 424/426

Primary Examiner—Thurman K. Page
Attorney, Agent, or Firm—John F. Sieberth

[57] ABSTRACT

A device for controlled release of one or more pharmacologically active substances within an animal which comprises (i) a body of a bioerodable solid state poly(amino acid ester) phosphazene polymer, and (ii) at least one pharmacologically active substance physically incorporated within said body. The device may comprise an implantable body in which the poly(amino acid ester)phosphazene polymer is a matrix within which such pharmacologically active substance is dispersed. Alternatively, the polymer may constitute a coating or container within which such pharmacologically active substance is physically encased—i.e., the polymer surrounds the active agent as in a capsule or in a microencapsulated form. Results of in vivo experiments using implants of poly[bis((ethyl glycino)phosphazene] containing 25% ethidium are described.

62 Claims, 2 Drawing Sheets

CUMULATIVE RELEASE OF DRUG, IN VITRO.

CUMULATIVE RELEASE OF DRUG, IN VITRO.

ETHIDIUM RELEASE PER ROD AND PER DAY AS FUNCTION OF TIME.

ETHIDIUM PLASMA CONCENTRATION IN T. CONGOLENSE-INFECTED RABBITS AFTER SUBCUTANEOUS IMPLANTATION OF ETHIDIUM-CONTAINING POLY [BIS(ETHYL GLYCINO) PHOSPHAZENE] RODS.

ETHIDIUM PLASMA CONCENTRATION IN NON-INFECTED RABBITS AFTER SUBCUTANEOUS IMPLANTATION OF ETHIDIUM-CONTAINING POLY [BIS(ETHYL GLYCINO) PHOSPHAZENE RODS.

BIOERODABLE SUSTAINED RELEASE IMPLANTS

TECHNICAL FIELD

This invention relates to devices for controlled release of one or more pharmacologically active substances within an animal, and the production and use of such devices.

BACKGROUND

One of the most frequently used controlled release systems consists of a biologically active agent physically incorporated in a polymeric matrix, shaped to a convenient form and implanted by injection. The rate of release of the active agent is then controlled by diffusion through the polymeric matrix, and is only weakly dependent on the external conditions. According to Fick's first law, the diffusion rate is proportional to the concentration gradient across the membrane and to the diffusion coefficient of the permeant in the matrix.

In the last decades the interest in using biodegradable polymers as matrix drug delivery has grown significantly for two essential reasons. First, the decline in release rate due to the depletion of the matrix can be compensated by the release of drug due to erosion of the polymer matrix. Second, the bioerosion of the polymer matrix avoids the difficult removal of the matrix by surgery. It is, however, important to note that a constant release is not always desirable. In many cases (for example, trypanocidal drugs) a high initial dose, followed by a constant or slowly declining drug release may produce the most desired therapeutic effect.

J. Heller, U.S. Pat. No. 4,639,366, describes a controlled release device comprising (a) a polymer with at least one labile backbone bond per repeat unit and at least one pendant acid functionality per thousand repeat units, and (b) a therapeutic or biologically active agent incorporated within or surrounded by the matrix of the polymer. These polymers may be prepared by reacting a polyol, preferably a diol, having a pendant acidic group with a polymer containing a labile backbone bond. Polymers mentioned for use in this reaction are polyorthoesters (including polyorthocarbonates), polyacetals, polyketals, polyesters and polyphosphazenes.

In U.S. Pat. No. 3,893,980 and in *Macromolecules*, 1977, Vol. 10, No. 4, pages 824–830, H. R. Allcock et al describe the synthesis of phosphazene high polymers with glycino ethyl ester, alanino methyl ester, leucino methyl ester, and phenylalanino methyl ester substituents by the interaction of poly(dichlorophosphazene) with amino acid esters. Total halogen replacement was achieved only with glycine ethyl ester. Replacement of the remaining chlorine could be effected by the subsequent introduction of methylamino groups as cosubstituents. The objective of this work was to determine whether the polymers could be biocompatible as solids or biodegradable to harmless hydrolysis products. If the products proved to be soluble in aqueous media, they could possibly be used as plasma extenders or carrier molecules for chemotherapeutic drugs. As pointed out in the patent, the methylamino groups were utilized in order to impart hydrophilicity to the polymers, a feature which was deemed by the patentees to be very important.

In *Journal of Controlled Release*, 1986, Vol. 3, pages 143–154, C. W. J. Grolleman et al describe the synthesis of bioerodible phosphazene polymers containing a model drug (phenylacetic acid) or a drug (naproxen) covalently bound to the chain through a spacer, L-lysine. Residual chlorine on the partially substituted polyphosphazene was replaced by reaction with glycine ethyl ester. Subsequent papers by Grolleman et al (Ibid., 1986, Vol. 4 pages 119–131; and pages 133–142) describe experiments in vitro and in vivo using such naproxen-substituted polyphosphazene drug release systems.

THE INVENTION

This invention provides, inter alia, a device for controlled release of one or more pharmacologically active substances within an animal which comprises (i) a body of a bioerodable solid state poly(amino acid ester)phosphazene polymer, and (ii) at least one pharmacologically active substance physically incorporated within said body. The device may comprise an implantable body in which the poly(amino acid ester)phosphazene polymer is a matrix within which such pharmacologically active substance is dispersed. Alternatively, the polymer may constitute a coating or container within which such pharmacologically active substance is physically encased—i.e., the polymer surrounds the active agent as in a capsule or in a microencapsulated form.

Bioerodable solid state poly(amino acid ester)phosphazene polymers which may be employed in the devices of this invention include those represented by the general formula $$[N=P(R-L)_{2x}(R''-OR')_{2y}]_n \qquad (I)$$

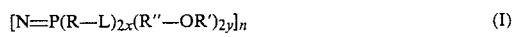

wherein R is the residue of an alpha-amino acid; R' is a hydrocarbyl group; R'' is the residue of an alpha-amino acid; n is from about 50 to about 25,000; and x is a number averaging from 0.05 to 1.00 (preferably 0.05 to 0.95) per repeating unit and y is a number averaging from 0.95 to 0.00 (preferably 0.95 to 0.05) per repeating unit so that per repeating unit the sum of x and y is 1; and L is $R_1OR_2$ or $OCH(R_3)COOR_4$ or $OR_5$ in which $R_1$ is the residue of an alpha-amino acid, $R_2$, $R_4$ and $R_5$ are hydrocarbyl groups, and $R_3$ is a hydrogen atom or a hydrocarbyl group.

One subgroup of these polymers may be represented by the general formula $$[N=P(R-R_1OR_2)_{2x}(GlyOR')_{2y}]_n \qquad (II)$$

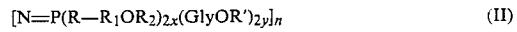

wherein R and $R_1$ can be the same or different and each is a residue of an alpha-amino acid; $R_2$ and R' can be the same or different and each is a hydrocarbyl group; n is from about 50 to about 25,000; and x is a number averaging from 0.05 to 1.00 (preferably 0.05 to 0.95) per repeating unit and y is a number averaging from 0.95 to 0.00 (preferably 0.95 to 0.05) per repeating unit so that per repeating unit the sum of x and y is 1.

Another subgroup of these polymers may be represented by the general formula $$[N=P(R-OCH(R_3)COOR_4)_{2x}R''OR')_{2y}]_n \qquad (III)$$

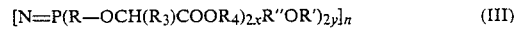

wherein R and R'' can be the same or different and each is a residue of an alpha-amino acid; $R_3$ is a hydrogen atom or a hydrocarbyl group; $R_4$ and R' can be the same or different and each is a hydrocarbyl group; n is from about 50 to about 25,000; and x is a number averaging from 0.05 to 1.00 (preferably 0.05 to 0.95) per repeating unit and y is a number averaging from 0.95 to 0.00 (preferably 0.95 to 0.05) per repeating unit so that per repeating unit the sum of x and y is 1.

Yet another subgroup of useful polymers is represented by the general formula $$[N=P(R-OCH(R_3)COOR_4)_{2x}(GlyOR')_{2y}]_n \qquad (IV)$$

wherein R is a residue of an alpha-amino acid; $R_3$ is a hydrogen atom or a hydrocarbyl group; $R_4$ and R' can be the same or different and each is a hydrocarbyl group; n is from about 50 to about 25,000; and x is a number averaging from 0.05 to 0.95 per repeating unit and y is a number averaging from 0.95 to 0.05 per repeating unit so that per repeating unit the sum of x and y is 1.

Still another subgroup of useful polymers is represented by the general formula $$[N=P(R-OR_5)_{2x}(R''-OR')_{2y}]_n \qquad (V)$$

wherein R and R'' are residues of at least two different alpha-amino acids; $R_5$ and R' can be the same or different and each is a hydrocarbyl group; n is from about 50 to about 25,000; and x is a number averaging from 0.05 to 0.95 per repeating unit and y is a number averaging from 0.95 to 0.05 per repeating unit so that per repeating unit the sum of x and y is 1.

Another type of useful polymers are those represented by the general formula $$[N=P(R-OCH(R_3)COOR_4)_{2x}(NR_6R_7)_{2y}]_n \qquad (VI)$$

wherein R is a residue of an alpha-amino acid; $R_4$ and $R_6$ can be the same or different and each is a hydrocarbyl group; each of $R_3$ and $R_7$ is independently a hydrogen atom or a hydrocarbyl group, n is from about 50 to about 25,000; and x is a number averaging from 0.05 to 0.95 per repeating unit and y is a number averaging from 0.95 to 0.05 per repeating unit so that per repeating unit the sum of x and y is 1.

A preferred subgroup of polymers of Formula (I) above wherein L is $R_1OR_2$ as therein defined, may be prepared by (a) reacting a dipeptide ester with a dihalophosphazene polymer in a liquid reaction solvent and in the presence of a hydrogen halide acceptor to effect partial substitution of the halogen of the dihalophosphazene polymer by dipeptide ester groups and thereby form a partially substituted polymer; and (b) reacting the partially substituted polymer with a glycine ester in a liquid reaction solvent and in the presence of a hydrogen halide acceptor to effect substitution of the remaining halogen of the partially substituted polymer by glycine ester groups.

Another preferred subgroup of polymers of Formula (I) above wherein L is $OCH(R_3)COOR_4$ as therein defined, may be produced by a process which comprises (a) reacting a protected alpha-amino acid or salt thereof with an alpha-haloalkanoic acid ester in a liquid reaction solvent and in the presence of a tertiary amine to effect alkylation of the protected alpha-amino acid and formation of a protected amino acid ester of the formula $$Z-NH-R_8-OCH(R_3)COOR_4 \qquad (VII)$$

wherein Z is the protecting group, NH—$R_8$ is the residue of the alpha-amino acid, $R_3$ is a hydrogen atom or a hydrocarbyl group, and $R_4$ is a are hydrocarbyl group; (b) removing the protecting group and reacting the amino acid ester with a dihalophosphazene polymer in a liquid reaction solvent and in the presence of a hydrogen halide acceptor to effect partial substitution of the halogen of the dihalophosphazene polymer by amino acid ester groups and thereby form a partially substituted polymer; and (c) reacting the partially substituted polymer with a glycine ester in a liquid reaction solvent and in the presence of a hydrogen halide acceptor to effect substitution of the remaining halogen of the partially substituted polymer by glycine ester groups.

Still another preferred subgroup of polymers of Formula (I) above wherein L is $OR_5$ as therein defined, are formed by use of the following procedures: When R in Formula (I) above is Gly, the polymers can be prepared by reacting one or more glycine esters with a dihalophosphazene polymer in a liquid reaction solvent and in the presence of a hydrogen halide acceptor. Provided the ester group $OR_5$ is sufficiently small as not to give rise to steric hindrance, essentially all of the halogen on the dihalophosphazene polymer can be replaced by $GlyOR_5$ groups. When R in Formula (I) above is other than Gly, the polymers are readily prepared by (a) reacting an alpha-amino acid ester in which the acid has more than two carbon atoms in the molecule with a dihalophosphazene polymer in a liquid reaction solvent and in the presence of a hydrogen halide acceptor to effect partial substitution of the halogen of the dihalophosphazene polymer by alpha-amino acid ester groups and thereby form a partially substituted polymer; and (b) reacting the partially substituted polymer with a glycine ester in a liquid reaction solvent and in the presence of a hydrogen halide acceptor to effect substitution of the remaining halogen of the partially substituted polymer by glycine ester groups.

In the operations described above in which an amino-acid ester is reacted with a dihalophosphazene polymer or a partially substituted dihalophosphazene polymer, the reaction may be conducted in any of a variety of solvents such as tetrahydrofuran, dimethoxyethane, diglyme, triglyme, toluene, xylene, cyclohexane, 1,4-dioxane, chloroform, methylene chloride, chlorobenzene, dichlorobenzene, tetrachloroethane, and the like, including mixtures of two or more such solvents or a mixture of one or more such solvents with acetonitrile, acetone, diethylethylketone, etc. The solvent employed should have the capability of keeping the dihalophosphazene polymer, the amino acid ester, and the polymer product in solution.

Of the dihalophosphazene polymers, poly(dichlorophosphazenes) are preferred, although poly(difluorophosphazene) and poly(dibromophosphazene) can be used. When the fully substituted amino ester polymer is to be used in making implants by melt extrusion techniques, it is desirable to use in the synthesis relatively low molecular weight dihalophosphazene polymers and to select the amino esters so as to provide suitable melt viscosities at extrusion temperatures below about 150° C.

Among the hydrogen halide acceptors that may be utilized in these reactions are tertiary amines such as trimethylamine, triethylamine, tripropylamine, tributylamine, trihexylamine, tetramethylethylene diamine, 1,4-diazabicyclo[2.2.2]octane, pyridine, N-methylpyrrole, N-methylmorpholine; inorganic bases such as sodium carbonate, potassium carbonate, sodium bicarbonate, or potassium bicarbonate (provided the inorganic base is soluble in the particular solvent system used);

and the like. An excess of the amino substituted ester reactant may also serve as the hydrogen halide acceptor.

Relatively mild reaction conditions are generally used, with temperatures in the range of about 0° to about 60° C. being typical, and about 0° to about 25° C. preferred. With temperatures lower than 0° C., longer reaction times should be used, whereas with temperatures above about 25°–30° C., shorter reaction times are desirable to minimize the extent of crosslinking and hydrolytic chain cleavage that may possibly occur.

When forming amino acid esters of formula (VII) above, a protected alpha-amino acid or salt thereof is reacted with an alpha-haloalkanoic acid ester in a liquid reaction solvent of the type described, again using a hydrogen halide acceptor such as a tertiary amine. Temperatures in the range of 20° to 125° C. are typical. To remove the protecting group, various procedures may be used depending upon the type of protecting group employed. With groups such as the carbobenzyloxycarbonyl protecting group catalytic hydrogenation in an alcoholic medium in the presence of a dibasic acid such as oxalic acid is particularly efficacious.

Examples of poly(amino acid ester)phosphazene polymers that may be used include

[N=P(GlyGlyOR$_2$))$_{2x}$(GlyOR')$_{2y}$]$_n$
[N=P(GlyAlaOR$_2$))$_{2x}$(GlyOR')$_{2y}$]$_n$
[N=P(GlyLeuOR$_2$))$_{2x}$(GlyOR')$_{2y}$]$_n$
[N=P(GlyPheOR$_2$))$_{2x}$(GlyOR')$_{2y}$]$_n$
[N=P(GlyOCH$_2$COOR$_4$)$_{2x}$(GlyOR')$_{2y}$]$_n$
[N=P(GlyOCH(CH$_3$)COOR$_4$)$_{2x}$(GlyOR')$_{2y}$]$_n$
[N=P(GlyOR$_5$)$_{2x}$(GlyOR')$_{2y}$]$_n$
[N=P(LeuOR$_5$)$_{2x}$(GlyOR')$_{2y}$]$_n$
[N=P(PheOR$_5$)$_{2x}$(GlyOR')$_{2y}$]$_n$ wherein R, R', R$_4$ and R$_5$ are, independently, alkyl, alkenyl, cycloalkyl, aryl, aralkyl, or the like, preferably lower alkyl groups, and most preferably ethyl groups; and x, y and n are as defined above.

A few particularly preferred polymers include

[N=P(GlyGlyOEt))$_{2x}$(GlyOEt)$_{2y}$]$_n$; x=0.3 & y=0.7
[N=P(GlyAlaOEt))$_{2x}$(GlyOEt)$_{2y}$]$_n$; x=0.85–0.9 & y=0.15–0.1
[N=P(GlyLeuOEt))$_{2x}$(GlyOEt)$_{2y}$]$_n$; x=0.85–0.9 & y=0.15–0.1
[N=P(GlyPheOEt))$_{2x}$(GlyOEt)$_{2y}$]$_n$; x=0.75–0.8 & y=0.25–0.2
[N=P(GlyOCH(CH$_3$)COOEt)$_{2x}$(GlyOEt)$_{2y}$]$_n$; x=0.45 & y=0.55
[N=P(GlyOCH(CH$_3$)COOEt)$_{2x}$(GlyOEt)$_{2y}$]$_n$; x=0.25 & y=0.75
[N=P(GlyOCH(CH$_3$)COOEt)$_{2x}$(GlyOEt)$_{2y}$]$_n$; x=0.10 & y=0.90
[N=P(LeuOEt)$_{2x}$(GlyOEt)$_{2y}$]$_n$; x=0.45 & y=0.55
[N=P(PheOEt)$_{2x}$(GlyOEt)$_{2y}$]$_n$; x=0.75 & y=0.25

In the above particularly preferred polymers, x and y represent values experimentally determined by 360 or 500 MHz $^1$H—NMR spectroscopy.

Typical pharmacologically active materials that may be physically incorporated in bioerodable poly(amino acid ester)-phosphazenes such as those referred to above include Trypanocides, such as ethidium.
Antibiotics/antibacterials, such as the tetracyclines.
Antiparasitics, such as the avermectins (e.g., ivermectin), diethyl carbamazine.
Non-steroidal antiinflammatories, such as flunixen.
Growth permittants.
Steroid hormones, such as testosterone, estradiol.
Growth hormones, such as zeranol, bovine somatotropin.
Estrus synchronizers, such as estrogens, progestins (e.g., progesterone).

The ensuing examples illustrate the practice and advantages of this invention.

EXAMPLE 1

Figure 2:
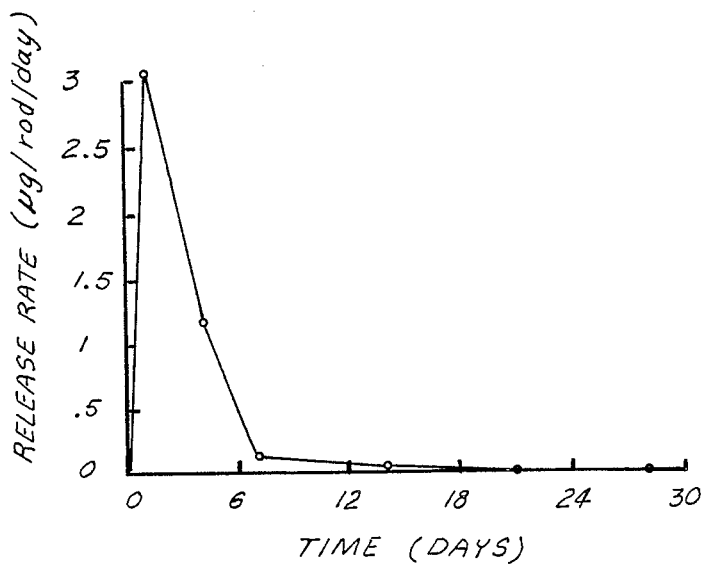

Ethidium (1 g, Homidium bromide) and poly[bis-(ethyl glycino)phosphazene] (3 g) were transferred into a 100 mL silanized glass flask containing 40–50 mL dry chloroform. This mixture was stirred in an ultrasonic bath for 10–15 hours under an atmosphere in polymer solution was poured out into 15 cm silanized petri-dishes. After one hour drying at room temperature a film polymer was formed. The film was then dried in vacuum for 5 hours. (Note: Other volatile polymer solvents may be used, such as THF, benzene, methylene chloride, toluene, etc., and the evaporation of the solvent can be improved by heating the petri-dishes at 30°–40° C. and/or by vacuum evaporation of the solvent in a desiccator.) Dry films of the poly[bis(ethyl glycino)phosphazene] containing 25% by weight of ethidium were then ground into a powder. The powder was melt extruded through a 1.2–1.8 mm die at temperatures ranging from 90°–115° C. and pressures between 200 and 750 psi. (Extrusion temperatures over 150°–175° C. resulted in intense thermal degradation both of the drug and the polymer.) The resultant strands had diameters of 1.2–2 mm depending on the extrusion temperature and pressure used. Rods 1 cm in length (30 mg each) cut from strands 1.70 mm in diameter were maintained in a Sorensen buffer (pH 7.4) at 37° C. At regular intervals, the buffer solution was replaced and analyzed for ethidium by means of HPLC. The results of these tests are shown graphically in FIGS. 1 and 2.

EXAMPLE 2

Rods formed as in Example 1, sterilized in an ethylene oxide chamber, were subcutaneously implanted (four per animal) by injection in the thorax in rabbits, just behind the shoulder. In these tests, rabbits infected with T. congolense trypanosomes and non-infected rabbits were studied. In order to study the bioacceptability of the implanted poly[bis(ethyl glycino)phosphazene]polymer, rods of the same size and polymer, but devoid of ethidium were likewise implanted in rabbits. In order to evaluate the prophylactic activity of the matrixes containing ethidium, the rabbits were reinfected with different strains of Trypanosoa congolense during the experiments. The implantation and parasitemia data are reported in Table I.

Some rabbits were sacrificed at the end of the experiment in order to examine the implantation site for possible tissue reaction and to check the effect of the implantation on the formulations. No or very little reaction was observed around the implants devoid of ethidium. At most a very small membrane was formed around the implant. There was more tissue reaction around the implants which contained the ethidiuri. In this case the rods themselves were damaged and sometimes only pieces of them were found. This reaction was probably caused by the high initial release of the ethidium from the implants.

Figure 3:
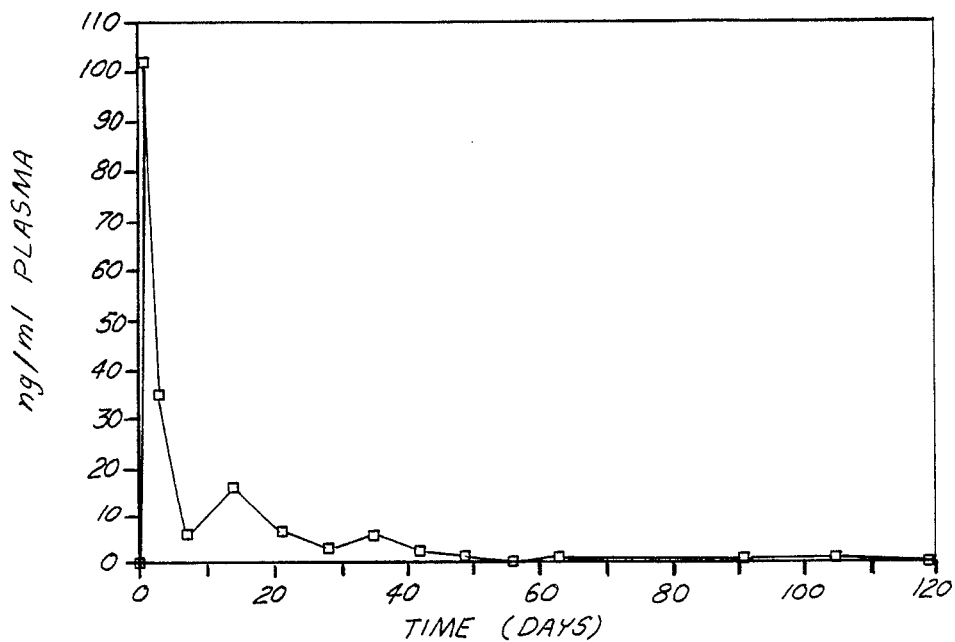
Figure 4:
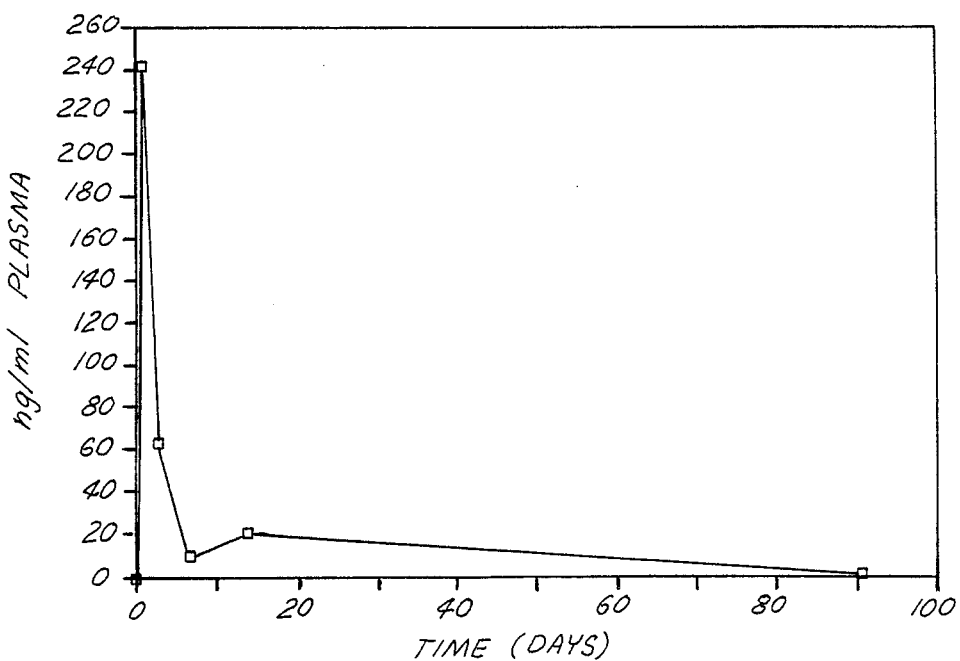

At different time intervals during these experiments, blood samples were withdrawn and analyzed for ethidium. The analytical technique used to detect Homidium bromide levels in rabbit serum was developed by Perschke and Vollnert, *Acta Tropica*, 1985, Vol. 42, pages 209–216. Ethidium plasma concentrations as detected by this analytical method are shown in Table II and are plotted in FIGS. 3 and 4.

TABLE I

Effect of Ethidium-Poly[bis(ethyl glycino)phosphazene] Implants in a Program Involving Infection of Rabbits with *T. Congolense* Trypanosomes

| DAYS | No. 1 | No. 2 | No. 3 | No. 4 | Blank 1 | Blank 2 |
|---|---|---|---|---|---|---|
| 0 | 4.3; I | 5.4; I | 5.5; I | 2.9 | 2.7 | 2.5 |
| 7 | (<1) | (<1) | (<1) | | | |
| 14 | (<1) | (1) | (10) | | I | |
| 22 | (4–6) | (1) | (4–6) | | (8–12) | |
| 28 | T | T | T | T | $T_{bl}$ | $T_{bl}$ |
| 29 | 4.2;(1);+ | 5.3;(<1);− | 5.7;(<1);− | 3.5 | 2.8;(4–6) | |
| 31 | (<1);− | (<1);− | (<1);− | | (4–6) | |
| 35 | 4.5 | 5.2 | 5.9 | 3.6 | EXP | |
| 42 | 4.6;(<1);− | 5.2;(<1);− | 5.8;(<1);− | | | |
| 56 | 3.9;(<1) | 4.5;(<1) | 4.8;(<1) | 2.75 | | 2.1 |
| 62 | [*] | | | | | [**] |
| 63 | 4.5;(<1) | 5.3;(<1) | 5.6;(<1) | | | |
| 70 | 4.7;(<1);− | 5.5;(<1);− | 5.9;(<1);− | 3.8 | | |
| 77 | (<1);− | (<1);− | (<1);− | | | |
| 79 | 5.1; I-2 | 5.8; I-2 | 6.1; I-2 | | | |
| 85 | 5.0;(<1) | 5.7;(<1) | 6.1;(<1) | | | |
| 91 | 4.9;(<1) | 5.4;(<1) | 6.2;(<1) | | | |
| 98 | 5.2;(<1) | 5.6;(<1) | 6.3;(<1) | | | |
| 106 | 5.0;(<1) | 5.8;(<1) | 6.2;(<1) | 4.0 | | |
| 119 | 5.2;(<1) | 6.5;(<1) | | | | |
| 120 | I-3 | I-3 | I-3 | | | |
| 133 | 5.4;(<1) | 5.6;(<1) | 4.5;(<1) | | | |
| 141 | (<1);− | (4–6);+ | | | | |
| 146 | 5.6;− | EXP | 6.3;+ | | | |
| 160 | 5.8;− | | 6.2;− | 4.7 | | |
| 168 | I-4 | | | | | |
| 175 | 5.9;(<1);− | | 5.8;(1);+ | 4.9 | | |
| 189 | 6.1;(<1);− | | 5.4;+;CT | 5.0 | | |

On Day 203 Rabbit No. 1 was still negative.
Legend for Table I:
Underscored numbers = weights in kg
I = Infected with *T. congolense*, intraperitoneal injection of 0.5 mL of blood of an infected mouse (parasitemia = 160)
( ) = Parasitemia expressed as the amount of trypanosomes per 20 investigated microscopic fields (at 400x magnification)
T = Subcutaneous implantation of 4 ethidium containing polymer rods (i.e. Treatment)
$T_{bl}$ = Subcutaneous implantation of 4 blank polymer rods
+ or − = Positive or negative Buffycoat capillary test (Heamat. tubes)
I-2 = Reinfected with a mixture of two different *T. congolense*, popul. R 111 and R 109
EXP = Died of trypanosomiasis
I-3 and I-4 = Reinfected with *T. congolense Boma*
CT = Experiment ended as the rabbit had chronic Trypanosomiases
[*] = Attempted to remove one rod surgically; reaction tissue observed around the rod; the rod itself was damaged
[**] = No or very little tissue reaction observed around the implanted rods

TABLE II

Ethidium concentration (ng/ml), as detected by HPLC analysis, of the serum of *T congolense* infected rabbits (1, 2, 3) and non-infected (4) treated with subcutaneous implantation of polyphosphazene based ethidium delivery systems.

| DAYS AFTER TREATMENT | 1 | 3 | 7 | 14 | 21 | 28 |
|---|---|---|---|---|---|---|
| ANIMAL | | | | | | |
| 1 | 119.0 | 35.4 | POOLED | POOLED | POOLED | POOLED |
| 2 | 117.6 | 31.3 | " | " | " | " |
| 3 | 69.6 | 38.6 | " | " | " | " |
| AVERAGE | 102.0 | 35.1 | 6 | 16 | 6.5 | 3 |
| 4 | 242 | 63 | 9 | 20 | N D | M |

| DAYS AFTER TREATMENT | 35 | 42 | 49 | 56 | 63 | 91 | 105 | 119 | 133 |
|---|---|---|---|---|---|---|---|---|---|
| ANIMAL | | | | | | | | | |
| 1 | POOLED | POOLED | POOLED | 0.5 | 0.7 | 0.8 | 0.7 | N D | N D |
| 2 | " | " | " | 0.35 | N D | 0.8 | S C | M | M |
| 3 | " | " | " | 0.3 | 0.5 | 0.45 | S C | 0.3 | N D |
| AVERAGE | 5.5 | 2.3 | 1.2 | 0.4 | 0.6 | 0.7 | 0.7 | 0.3 | N D |
| 4 | M | M | M | M | 1.4 | S C | N D | N D | |

TABLE II-continued

Ethidium concentration (ng/ml), as detected by HPLC
analysis, of the serum of *T congolense* infected rabbits
(1, 2, 3) and non-infected (4) treated with
subcutaneous implantation of polyphosphazene based
ethidium delivery systems.

with improved analytical method

M = sample missing
N D = not detectable
S C = sample clotted

Table I shows that the subcutaneous implantation of the poly[bis(ethyl glycino)phosphazene] delivery systems containing the ethidium (in rabbits 1 to 3) was therapeutically effective against the pre-established T. congolense infection. Moreover a prophylactic action of the drug persisted over a significant period of time. None of the rabbits was positive after reinfection (I-2) with another two different strains of T. congolense made on day 49 after the implantation. In contrast, the infected animal (Blank 1) treated with four blank polymer rods died 21 days after the T. congolense infection. A second reinfection (rabbits 1-3) with a new strain of T. congolense Boma (isolated in 1987 in a Zairian population) appeared to be fatal for two of the rabbits, but not for rabbit 1.

These results are generally supported by the analysis of serum ethidium concentrations (Table II, FIGS. 3 and 4) The average ethidium concentration in the blood declined rapidly during the first days after the implantation. This initial fast release was followed by a slow decline of the ethidium concentration over a considerable period of time. Comparison of FIGS. 3 and 4 (rabbits 1-2-3 average v. rabbit 4) shows that the ethidium plasma concentration was much higher in the non-infected treated rabbit. This difference can be explained by the intense assimilation of ethidium by the trypanosories—see Gilbert and Newton, *Parasitology*, 1982, Vol. 85, pages 127-148. Even after 91 days this absorption effect was still observed—see Table II.

Comparison of the above in vivo results with the levels observed after intramuscular injection of ethidium at the level of 1 ng/kg reported by Gilbert and Newton (loc. cit.) shows that the drug level by the intramuscular injection method of administration was very low even after only two days.

EXAMPLE 3

Synthesis of $[NP(GlyGlyOEt)_{2x}(GlyOEt)_{2y}]_n$

A suspension of dry glycyl-glycine ethyl ester hydrochloride (3.73 g; 0.0177 mole) and dry purified triethylamine (TEA) (2.45 mL; 0.0177 mole) is stirred in dry boiling benzene (125 mL) for 90 minutes. The mixture is then cooled to room temperature and filtered under an atmosphere of dry nitrogen to remove TEAH+Cl−. The filtrate is transferred into a 500 mL flask containing 1.25 mL TEA (0.009 mole) and cooled with ice. To this a solution of 0.51 g (0.00443 mole NPCl₂) (4.3 mL of a 12% solution in cyclohexane) in 50 mL benzene is added dropwise under N₂-atmosphere. The mixture is stirred at 0° C. for 4 hours and subsequently at 25° C. for an additional 15 hours. Meanwhile dried glycine ethyl ester hydrochloride (3.09 g; 0.22 mole) is transferred into a 100 mL flask containing dry benzene (40 mL) and TEA (3.08 mL). The mixture is stirred and refluxed for 3.5 hours and is then cooled to room temperature and filtered (TEAH+Cl−) When reaction of GlyGlyOEt with $[NPCl_2]_n$ has been completed, the prepared glycine ethyl ester solution in benzene is added to this reaction mixture. The solution is stirred for an additional 6 hours at 0° C. and at 25° C. for 16 hours. After removal of the insoluble hydrochloride salt by filtration, the polymer solution is concentrated by vacuum evaporation of solvent at 30°–35° C. Dropwise addition of this concentrate into 300 mL dry n-heptane yields a solid white polymer. This is then reprecipitated from dry CHCl₃ into 300 mL n-heptane and again into 300 mL dry ether. The proportions of the substituents in the resultant polymer as determined by 360 MHz ¹H—NMR spectroscopy are $[NP(GlyGlyOEt)_{0.6}(GlyOEt)_{1.4}]_n$. This polymer is melt extrudable at 60°–100° C. and at pressures of 5–10 psi through a 1.2–1.8 mm die whereby smooth strands are formed.

The foregoing disclosure has been presented for purposes of illustration and not limitation. As can readily be appreciated by those skilled in the art, this invention is susceptible to considerable variation in its practice within the spirit and scope of the ensuing claims.

We claim:

1. A device for controlled release of one or more pharmacologically active substances within an animal which comprises
   (i) a bioerodable solid state poly(amino acid ester)-phosphazene polymer represented by the general formula $[N—P(R—L)_{2x}(R''—OR')_{2y}]_n$ wherein R is the residue of an alpha-amino acid, R' is a hydrocarbyl group, R'' is the residue of an alpha-amino acid, n is from about 50 to about 25,000, and x is a number averaging from 0.05 to 1.00 per repeating unit and y is a number averaging from 0.95 to 0.00 per repeating unit so that per repeating unit the sum of x and y is 1, and wherein L is $R_1OR_2$, $OCH(R_3)COOR_4$, or $OR_5$ in which $R_1$ is the residue of an alpha-amino acid, $R_2$, $R_4$, and $R_5$ are hydrocarbyl groups, and $R_3$ is a hydrogen atom or a hydrocarbyl group; and
   (ii) at least one pharmacologically active substance physically incorporated within said polymer, said pharmacologically active substance comprising a trypanocide, antibiotic/antibacterial, antiparasitic, non-steroidal antiinflammatory, growth permittant, steroid hormone, growth hormone, or estrus synchronizer.

2. A device of claim 1 wherein said bierodable solid state polymer is a matrix within which such pharmacologically active substance is dispersed.

3. A device of claim 1 wherein said bioerodable solid state polymer is a coating or container within which such pharmacologically active substance is physically incorporated.

4. A device of claim 1 wherein the pharmacologically active substance is a trypanocide.

5. A device of claim 1 wherein the pharmacologically active substance is ethidium.

6. A device of claim 1 wherein said polymer is poly[bis(ethyl glycino)phosphazene].

7. A device of claim 1 wherein said polymer is poly[bis(ethyl glycino)phosphazene] and the pharmacologically active substance is ethidium.

8. A device of claim 1 wherein said polymer is a matrix of poly[bis(ethyl glycino)phosphazene] within which ethidium is dispersed.

9. A device for controlled release of one or more pharmacologically active substances within a living body which comprises
(i) a bioerodable solid state poly(amino acid ester)-phosphazene polymer of the general formula $$[N=P(R-L)_{2x}(GlyOR')_{2y}]_n$$

wherein R is the residue of an alpha-amino acid, R' is a hydrocarbyl group, n is from about 50 to about 25,000, and x is a number averaging from 0.05 to 0.95 per repeating unit and y is a number averaging from 0.95 to 0.05 per repeating unit so that per repeating unit the sum of x and y is 1, and wherein L is $R_1OR_2$, $OCH(R_3)COOR_4$, or $OR_5$ in which $R_1$ is the residue of an alpha-amino acid, $R_2$, $R_4$, and $R_5$ are hydrocarbyl groups, and $R_3$ is a hydrogen atom or a hydrocarbyl group; and
(ii) at least one pharmacologically active substance physically incorporated in said polymer, said pharmacologically active substance comprising a trypanocide, antibiotic/antibacterial, antiparasitic, non-steroidal antiinflammatory, growth permittant, steroid hormone, growth hormone, or estrus synchronizer.

10. A device of claim 9 wherein L is $R_1OR_2$ as therein defined.

11. A device of claim 10 wherein R and $R_1$ are both Gly.

12. A device of claim 10 wherein R is Gly and $R_1$ is Ala.

13. A device of claim 10 wherein R is Gly and $R_1$ is Leu.

14. A device of claim 10 wherein R is Gly and $R_1$ is PHe.

15. A device of claim 10 wherein R' and $R_2$ are both lower alkyl groups.

16. A device of claim 10 wherein R' and $R_2$ are both ethyl groups.

17. A device of claim 10 wherein R and $R_1$ are both Gly and R' and $R_2$ are both lower alkyl groups.

18. A device of claim 10 wherein R and $R_1$ are both Gly and R' and $R_2$ are both ethyl groups.

19. A device of claim 18 wherein x is about 0.3 and y is about 0.7 as determined by 360 MHz $^1$H—NMR spectroscopy.

20. A device of claim 10 wherein R is Gly and $R_1$ is Ala and R' and $R_2$ are both lower alkyl groups.

21. A device of claim 10 wherein R is Gly and $R_1$ is Ala and R' and $R_2$ are both ethyl groups.

22. A device of claim 21 wherein x is about 0.85–0.9 and y is about 0.15–0.1 as determined by 350 MHZ $^1$H—NMR spectroscopy.

23. A device of claim 10 wherein R is Gly and $R_1$ is Leu and R' and $R_2$ are both lower alkyl groups.

24. A device of claim 10 wherein R is Gly and $R_1$ is Leu and R' and $R_2$ are both ethyl groups.

25. A device of claim 24 wherein x is about 0.85–0.9 and y is about 0.15–0.1 as determined by 360 MHz $^1$H—NMR spectroscopy.

26. A device of claim 10 wherein R is Gly and $R_1$ is Phe and R' and $R_2$ are both lower alkyl groups.

27. A device of claim 10 wherein R is Gly and $R_1$ is Phe and R' and $R_2$ are both ethyl groups.

28. A device of claim 27 wherein x is about 0.75–0.8 and y is about 0.25–0.2 as determined by 360 MHZ $^1$H—NMR spectroscopy.

29. A device of claim 9 wherein L is $OCH(R_3)COOR_4$ as therein defined.

30. A device of claim 29 wherein R is Gly.

31. A device of claim 29 wherein $R_3$ is lower alkyl.

32. A device of claim 29 wherein $R_3$ is methyl.

33. A device of claim 29 wherein R' and $R_4$ are both lower alkyl groups.

34. A device of claim 29 wherein R' and $R_4$ are both ethyl groups.

35. A device of claim 29 wherein R is Gly and R' and $R_4$ are both lower alkyl groups.

36. A device of claim 29 wherein R is Gly and R' and $R_4$ are both ethyl groups.

37. A device of claim 29 wherein R is Gly and $R_3$ is lower alkyl.

38. A device of claim 29 wherein R is Gly and $R_3$ is methyl.

39. A device of claim 29 wherein R is Gly and R', $R_3$ and $R_4$ are lower alkyl groups.

40. A device of claim 29 wherein R is Gly, $R_3$ is methyl, and R' and $R_4$ are lower alkyl groups.

41. A device of claim 29 wherein R is Gly, $R_3$ is methyl, and R' and $R_4$ are both ethyl groups.

42. A device of claim 41 wherein x is about 0.10–0.50 and y is about 0.90–0.50 as determined by 360 MHz $^1$H—NMR spectroscopy.

43. A device of claim 9 wherein L is $OR_5$ as therein defined.

44. A device of claim 43 wherein R is Gly.

45. A device of claim 43 wherein R is Leu.

46. A device of claim 43 wherein R is Phe.

47. A device of claim 43 wherein R' and $R_5$ are both lower alkyl groups.

48. A device of claim 43 wherein R' and $R_5$ are both ethyl groups.

49. A device of claim 43 wherein R is Gly and R' and $R_5$ are both lower alkyl groups.

50. A device of claim 43 wherein R is Gly and R' and $R_5$ are both ethyl groups.

51. A device of claim 43 wherein R is Leu and R' and $R_5$ are both lower alkyl groups.

52. A device of claim 43 wherein R is Leu and R' and $R_5$ are both ethyl groups.

53. A device of claim 43 wherein R is Phe and R' and $R_5$ are both lower alkyl groups.

54. A device of claim 43 wherein R is Phe and R' and $R_5$ are both ethyl groups.

55. A device of claim 43 wherein R is Leu, x is about 0.45 and y is about 0.55 as determined by 360 MHz $^1$H—NMR spectroscopy.

56. A device of claim 43 wherein R is Phe, x is about 0.75 and y is about 0.25 as determined by 360 MHz $^1$H—NMR spectroscopy.

57. A device of claim 43 wherein R is Leu; R' and $R_5$ are both ethyl; and x is about 0.45 and y is about 0.55 as determined by 360 MHz $^1$H—NMR spectroscopy.

58. A device of claim 43 wherein R is Phe; R' and $R_5$ are both ethyl; and x is about 0.45 and y is about 0.55 as determined by 360 MHz $^1$H—NMR spectroscopy.

59. A device of claim 9 in the form of a body implant.

60. A device of claim 9 wherein the pharmacologically active substance is a trypanocide.

61. A device of claim 60 wherein the trypanocide is ethidium.

62. A device of claim 9 wherein the the polymer is poly[bis(ethylglycino)phosphazene] and the pharmacologically active substance is a trypanocide.

* * * * *

UNITED STATES PATENT AND TRADEMARK OFFICE
CERTIFICATE OF CORRECTION

PATENT NO. : 4,975,280
DATED : December 4, 1990
INVENTOR(S) : Etienne Schacht et al.

It is certified that error appears in the above-identified patent and that said Letters Patent is hereby corrected as shown below:

Column 11, line 45, reads "$R_1$ is PHe" and should read -- $R_1$ is Phe --.

Column 11, line 63, reads "by 350 MHZ" and should read -- by 360 MHz --.

Column 12, line 9, reads "360 MHZ" and should read -- 360 MHz --.

Signed and Sealed this

Fifteenth Day of September, 1992

Attest:

DOUGLAS B. COMER

*Attesting Officer*   *Acting Commissioner of Patents and Trademarks*